United States Patent
Högnelid et al.

[11] Patent Number: 6,095,138
[45] Date of Patent: Aug. 1, 2000

[54] PORTABLE RESPIRATION APPARATUS, AND SYSTEM EMPLOYING SAME

[75] Inventors: Kurt Högnelid, Bromma; Georgios Psaros, Tullinge, both of Sweden

[73] Assignee: Siemens Elema AB, Solna, Sweden

[21] Appl. No.: 09/078,018

[22] Filed: May 13, 1998

[30] Foreign Application Priority Data

May 16, 1997 [SE] Sweden .................................. 9701836

[51] Int. Cl.[7] .................................................. A61M 16/00
[52] U.S. Cl. .............................. 128/204.18; 128/204.21
[58] Field of Search ......................... 128/204.18, 204.22, 128/204.23, 204.25

[56] References Cited

U.S. PATENT DOCUMENTS

| | | | |
|---|---|---|---|
| 4,493,614 | 1/1985 | Chu et al. | 128/204.21 |
| 4,941,469 | 7/1990 | Adahan | 128/205.11 |
| 4,957,107 | 9/1990 | Sipin | 128/204.21 |
| 5,398,676 | 3/1995 | Press et al. | 128/204.23 |
| 5,452,713 | 9/1995 | Vipond et al. | 128/204.25 |
| 5,694,926 | 12/1997 | DeVries et al. | 128/205.24 |

FOREIGN PATENT DOCUMENTS

| | | |
|---|---|---|
| 0 284 543 | 9/1988 | European Pat. Off. . |
| 2 174 609 | 11/1986 | United Kingdom . |
| WO 96/11717 | 4/1996 | WIPO . |

*Primary Examiner*—John G. Weiss
*Attorney, Agent, or Firm*—Hill & Simpson

[57] ABSTRACT

A portable respiration apparatus is dimensioned to convey a flow of gas, with an upper limit on pressure, from an inlet to an outlet connected to a patient. The inlet of the portable respiration apparatus can be connected to a stationary gas unit when a higher pressure is desired. The stationary gas unit can generate a gas pressure that is applied to the inlet of the portable respiration apparatus, so that a higher gas pressure can be generated and delivered to the patient. Alternatively, the stationary gas unit can be dimensioned so that it is itself capable of generating the desired gas pressure to be supplied to the patient, so there is no additional increase in gas pressure in the portable respiration apparatus.

5 Claims, 1 Drawing Sheet

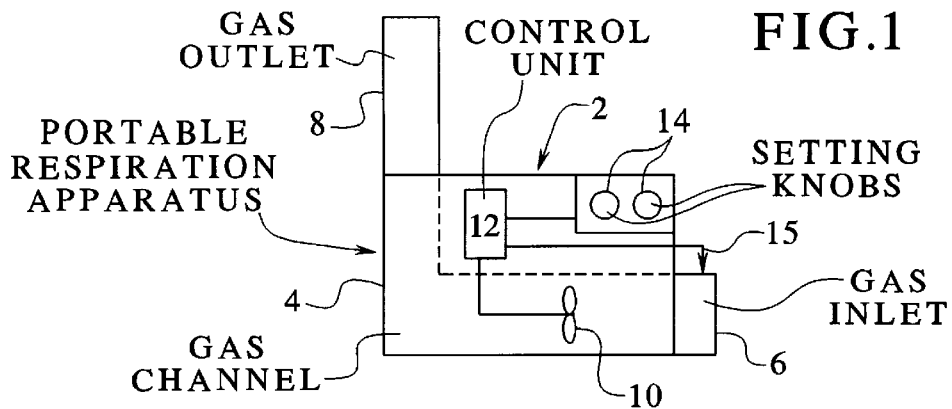
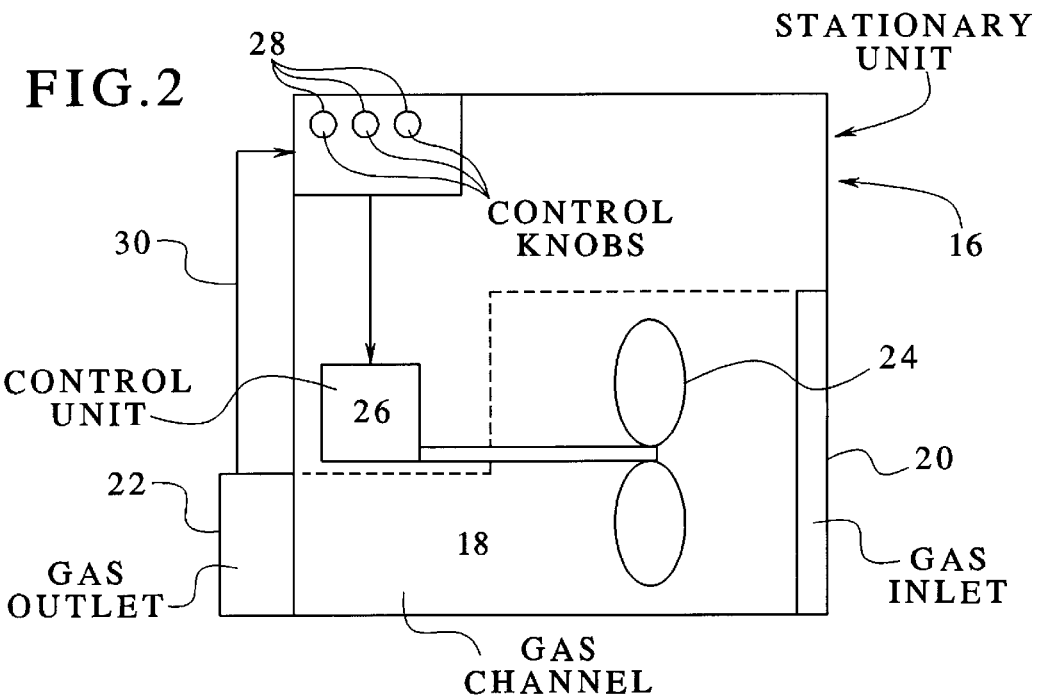
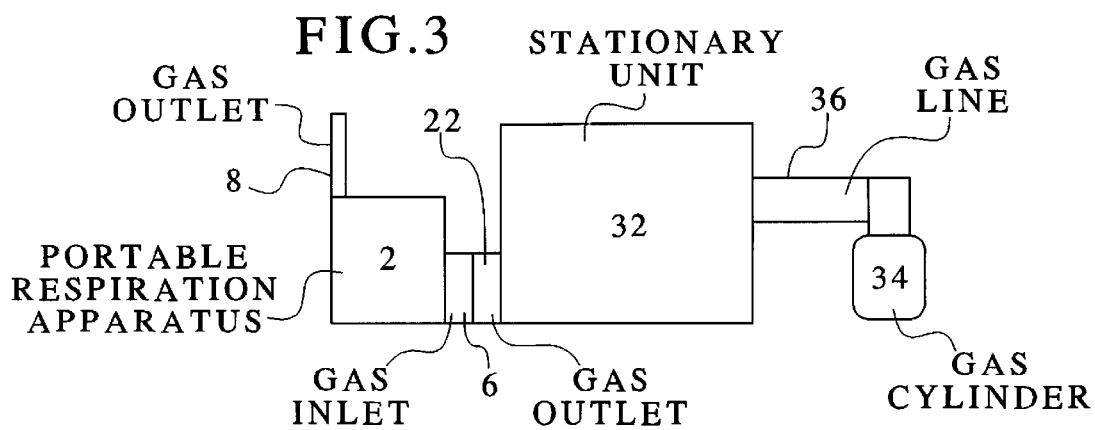

PORTABLE RESPIRATION APPARATUS, AND SYSTEM EMPLOYING SAME

BACKGROUND OF THE INVENTION

1. Field of the Invention

The present invention relates to a portable respiration apparatus, particularly a portable ventilator of the type having a pressure and flow generating unit with an inlet, and an outlet connectable to a patient.

The present invention also relates to a respiration apparatus system.

2. Description of the Prior Art

Simple types of ventilators (home care ventilators) intended for use in the home are available for many patients in need of limited assisted ventilation. These home ventilators often contain a compressor or fan for generating the required pressure of air supplied to the patient and sometimes even a small oxygen cylinder for enriching the oxygen content of the supplied air. Ventilators of this kind are also used in hospitals for e.g. subacute patients and in many developing countries. Utilization of these ventilators makes it possible to prevent the unnecessary occupation of expensive beds in intensive care.

One problem with these ventilators is the fact that they are relatively large and heavy, since a relatively large fan/compressor is needed to generate the full range of pressures that may be needed in treatment, i.e. up to about 100 cm $H_2O$. They also consume large amounts of energy. When the ventilators are battery-powered, the battery also contributes to increased ventilator weight and bulk. Even if they are transportable, usually mainly by being installed on different kinds of wheeled carriers, they are not particularly suitable for being carried by the patient.

A completely portable respiration apparatus would therefore offer the patient enormous freedom. One such apparatus can be achieved by miniaturizing the fan and by limiting the gas pressure that the apparatus is able to generate in relation to the available energy (a battery), e.g. by limiting pressure to about 40 to 60 cm $H_2O$. This pressure is sufficient for most patients in this category, especially patients who do not require supplemental oxygen or only a very small amount of supplemental oxygen (enabling a very small cylinder to last a relatively long time). The fan can then be completely battery-powered, and a smaller (rechargeable) battery will last long enough for the patient to be away from her/his home safely for a few hours, e.g. to go shopping or visit the doctor. When the patient returns home, or the battery needs recharging, the portable respiration apparatus is simply plugged into the nearest source of electrical power, such as the public mains (wall socket) or a car battery. The patient thus has almost unlimited mobility when traveling by car.

It should also be noted that the pressure-generating part of the portable respiration apparatus has a limited supply of energy, not necessarily a limited pressure-generating capacity. Miniaturization is solely for the purpose of minimizing battery size while still achieving a reasonably long period of time during which the portable respiration apparatus is able to run on battery power. When the portable respiration apparatus is used without any other source of energy except the battery for very brief periods of time, the portable respiration apparatus can be allowed to consume more energy and, accordingly, it can generate a higher pressure.

Nonetheless, even greater safety would be desirable to cover 30 every conceivable eventuality in which the supply of energy is limited or when the pressure-generating part of the respiration apparatus is technically restricted to the generation of a particular pressure, e.g. 40–60 cm $H_2O$.

In the latter instance, there is also the problem of accommodating patients in temporary need of a gas pressure higher than the portable ventilator is able to deliver.

One way to solve this problem would be to equip each patient with both a conventional home care ventilator and a portable respiration apparatus, however, the patient would then be forced to switch tubing to her/his airways and/or to the apparatus currently being used, as well as having to program both devices. This arrangement would also be more expensive overall, since both devices would have to be capable of independent operation.

SUMMARY OF THE INVENTION

An objective of the present invention is to provide a portable respiration apparatus of the type described above, but which avoids the aforementioned problems.

Another object of the invention is to provide a respiration apparatus system which solves the stated problems.

The above object is achieved in accordance with the principles of the present invention in a portable respiration apparatus having an air inlet and an air outlet connected between a pressure and flow generating unit, this unit producing a gas flow at the outlet which has an upper pressure limit. The outlet is adapted for connection to a patient for respirating the patient. The inlet is connectable to a stationary gas supply unit which supplies air or some other gas mixture with a predetermined flow and a positive pressure to the inlet. When the portable apparatus is connected to the stationary unit, a pressure which is higher than the upper pressure limit of the portable apparatus can be generated and gas can be supplied to the patient at this higher pressure.

The above object is also achieved in a respiration system employing a portable respiration apparatus as described above, connected to a stationary gas unit as described above.

When the portable respiration apparatus is devised so it can be connected to a stationary gas unit, an optimal system, consisting of a portable unit and a stationary unit, is achieved. The patient can easily take the portable unit anywhere and connect it, when necessary, to the stationary unit, which contributes sufficient "basic pressure" to enable the portable unit to supply an even higher pressure. Both units are specifically devised for their respective purposes and therefore can serve as a particularly cost-effective system, compared to the duplication of all functions that would be necessary if two completely separate devices, i.e. portable and stationary, had to be used. In principle, the portable unit contains all the control and regulatory functions.

It is especially advantageous for the portable unit's inlet to be adapted so that other independent units, such as conventional ventilators, could be connected to it. This can be done at a hospital where such devices are available. There is then no need for the patient to disconnect from the portable unit in order to undergo brief supplemental treatment with a ventilator, e.g. to permit the administration of some gas mixture other than ordinary air.

As used herein the term "stationary" unit does not necessarily refer to a permanently installed device but primarily to a separate pressure-generating unit that could also be portable. An interconnected system, i.e. a portable unit and a stationary unit, however, will always be somewhat bulkier than a portable unit alone. In principle, the portable unit could even be devised so that two portable units could be interconnected in order to increase pressure. A patient would therefore be able to have one stationary unit at home, one in the car, one at her/his work place etc. Ambulances, hospital beds etc. would be equipped with stationary units. The patient can then be simply and conveniently transported by different modes of transportation without any interruption in the breathing assistance provided.

DESCRIPTION OF THE DRAWINGS

FIG. 1 shows one embodiment of a portable respiration apparatus constructed in accordance with the invention.

FIG. 2 shows a first embodiment of a stationary unit constructed in accordance with the invention.

FIG. 3 shows the portable respiration apparatus connected to a second embodiment of a stationary unit, in accordance with the invention.

DESCRIPTION OF THE PREFERRED EMBODIMENTS

A portable respiration apparatus 2 is shown in FIG. 1. A gas channel 4 running through the portable respiration apparatus 2 between an inlet 6 and an outlet 8 carries a flow of air to a patient (not shown) via a system of tubing. The flow and pressure of the gas are generated by a fan 10 (which could 10 also be a turbine). The fan 10 is controlled by a control unit 12 which receives reference values for pressure and flow from setting knobs 14. The fan 10 can be dimensioned to generate a limited peak pressure, e.g. 40–60 cm $H_2O$, enabling the fan 10 to be made small enough for portability. These pressures are fully sufficient for a large percent of patients treated at home and offer them great freedom of movement. Some known turbines are small enough but still capable of generating up to about 130 cm $H_2O$, sufficient for any application. Energy requirements for the higher pressures, however, would then be so great so that an excessively large battery would be needed. Turbines are therefore functionally limited to generating only lower pressures during battery operation.

In instances in which a higher gas pressure is required, e.g. when the patient's condition takes a temporary change for the worse, a stationary unit can be connected to the inlet 6. A regulatory interface (illustrated with control line 15 from the control unit 12) can also be arranged at the inlet 6. FIG. 2 shows a first embodiment of a stationary unit 16. The stationary unit 16 has a gas channel 18 connecting an inlet 20 to an outlet 22. A fan 24 is arranged in the gas channel 18 to generate a flow of gas and positive pressure to the outlet 22. The fan 24 is controlled by a control unit 26 that receives reference values from control knobs 28 and/or from the portable unit via the control line 30.

A number of versions are possible here. The stationary unit 16 can be dimensioned so it only supplies the "differential pressure" for the portable unit's upper pressure limit, i.e. series connection of the pressure increase, the stationary unit 16 supplying a first pressure increase to a suitable level, e.g. about 60 cm $H_2O$, and the portable unit 2 supplying a second pressure increase, e.g. about 40 cm $H_2O$. The end pressure to the patient would then amount to about 70 cm $H_2O$ (only about 50% of the increase contributed by the stationary unit 16 would be achieved because of losses in the system in series connection).

Alternatively, the stationary unit 16 can be controlled from the portable unit 2 and made to supply the desired flow and pressure itself, the stationary unit 16 being dimensioned to be capable of generating up to e.g. 130 cm $H_2O$. This can easily be achieved, since the stationary unit 16 does not need to be dimensioned for space reasons in the same way as the portable unit 2. This also means that it is easier to retain dynamics across the entire pressure range with uncomplicated regulation, something that is not as simple with the series-connection alternative.

FIG. 3 shows the portable unit 2 connected to a second embodiment of the stationary unit 32. In this instance, the stationary unit 32 is formed basically as a regulator that can be set to reduce the pressure of gas from a gas cylinder 34 to an appropriate level. The portable unit 2 can then regulate the flow and end pressure to the patient from this basic pressure. The cylinder 34, which can contain any suitable gas mixture, is connected to the gas regulator 32 by a gas line 36. Ordinary air in particular can be connected.

In principle, the gas regulator 32 could be replaced with a conventional ventilator or a constant pressure-generating bellows system. Virtually any pressure-generating system can be employed for supplying the portable unit 2 with a basic level of pressure exceeding atmospheric pressure.

The interchangeability of the stationary unit 16 (or 32) offers numerous opportunities for making patients more comfortable and devising a rational system for providing acute, subacute and chronic patients with respiratory treatment and help.

In addition to the obvious benefits in home care, in which patient mobility is greatly improved, the principles of the system with a portable unit 2 and a stationary unit 16 (or 32) can also be applied to other applications, e.g. the transport of patients who need to be moved a number of times before reaching a treatment point at a hospital or the like. A patient can first be provided with a portable unit 2 as respiratory first aid. The portable unit 2 is connected to a stationary unit 16 (or 32) when the patient is placed in an ambulance (or some other appropriate vehicle). At the hospital, the portable unit 2 is disconnected from the stationary unit 16 (or 32), and the patient is transferred, retaining the portable unit 2 so there is no loss of breathing assistance, to a stretcher for further transportation to a treatment point.

In principle, the stationary unit 16 (or 32) can also be battery-powered and transported with the portable unit 2.

Another possible application is in anaesthesia where the patient needs breathing assistance during anaesthesia. This can also be performed on the way to the operating room. In principle, the induction of anaesthesia can be commenced during transportation to the hospital, e.g. by intravenous administration of an anaesthetic agent.

Although modifications and changes may be suggested by those skilled in the art, it is the intention of the inventors to embody within the patent warranted hereon all changes and modifications as reasonably and properly come within the scope of their contribution to the art.

We claim as our invention:

1. A respiration system comprising:
   a portable respiration apparatus having a gas inlet and a gas outlet and a pressure and flow generating unit, controlled by a portable respiration apparatus control unit, connected between said gas inlet and said gas outlet, said pressure and flow generating unit producing a gas flow having an upper pressure limit at said gas outlet from gas supplied at said gas inlet, and an intubation system connected to said gas outlet for supplying said gas flow from said gas outlet to a patient; and
   a stationary gas unit having a stationary gas unit inlet and a stationary gas unit outlet, said stationary gas unit outlet being releasably connectable to said gas inlet of said portable respiration apparatus, said stationary gas unit having gas supply means supplying gas to said gas inlet of said portable respiration apparatus having a predetermined flow and positive pressure and a control unit for operating said gas supply means for producing a gas flow at said gas outlet of said portable respiration apparatus having a pressure higher than said upper pressure limit; and said portable respiration apparatus being operable independently of said stationary gas unit.

2. A respiration system as claimed in claim 1 wherein said gas supply means comprises a stationary pressure and flow generating unit having said stationary gas unit inlet opening into ambient air and a fan for generating said predetermined positive pressure and for supplying gas at said predetermined positive pressure to said gas inlet of said portable respiration unit.

3. A respiration system as claimed in claim 1 wherein said gas supply means comprises a ventilator connected to a gas source containing gas under pressure.

4. A respiration system as claimed in claim 1 wherein said gas supply means comprises a gas source containing gas under pressure and wherein said control unit comprises a regulator for said gas source.

5. A respiration system as claimed in claim 1 wherein said gas supply means comprises means for generating a total flow of gas at an end pressure for delivery to a patient, and wherein said portable respiration unit comprises means for disconnecting said pressure and flow generating unit from said gas outlet of said portable respiration unit when said stationary gas unit outlet is connected to said gas inlet of said portable respiration unit.

* * * * *